US011491052B2

(12) United States Patent
Dewey et al.

(10) Patent No.: US 11,491,052 B2
(45) Date of Patent: Nov. 8, 2022

(54) NARROW ANGLE ILLUMINATION RING FOR OPHTHALMIC SURGICAL LASER SYSTEM

(71) Applicant: AMO DEVELOPMENT, LLC, Santa Ana, CA (US)

(72) Inventors: David A. Dewey, Sunnyvale, CA (US); Frank D. Fellenz, San Jose, CA (US); Tianheng Wang, Fremont, CA (US)

(73) Assignee: AMO Development, LLC, Irvine, CA (US)

( * ) Notice: Subject to any disclaimer, the term of this patent is extended or adjusted under 35 U.S.C. 154(b) by 0 days.

(21) Appl. No.: 17/058,654

(22) PCT Filed: Aug. 28, 2019

(86) PCT No.: PCT/IB2019/057247
§ 371 (c)(1),
(2) Date: Nov. 25, 2020

(87) PCT Pub. No.: WO2020/049417
PCT Pub. Date: Mar. 12, 2020

(65) Prior Publication Data
US 2021/0196512 A1 Jul. 1, 2021

Related U.S. Application Data

(60) Provisional application No. 62/726,939, filed on Sep. 4, 2018.

(51) Int. Cl.
*A61F 9/007* (2006.01)
*A61F 9/008* (2006.01)
(52) U.S. Cl.
CPC ............ *A61F 9/0079* (2013.01); *A61F 9/008* (2013.01)

(58) Field of Classification Search
CPC ........ A61F 9/007; A61F 9/0079; A61F 9/008; A61F 9/00804; A61F 9/00812;
(Continued)

(56) References Cited

U.S. PATENT DOCUMENTS

| 6,055,322 A * | 4/2000 | Salganicoff ............ A61B 3/156 |
| | | 382/117 |
| 7,927,344 B2 * | 4/2011 | Burba ..................... A61F 9/007 |
| | | 606/166 |

(Continued)

FOREIGN PATENT DOCUMENTS

| AU | 2010363107 A1 | 5/2013 |
| WO | 0175777 A1 | 10/2001 |

(Continued)

OTHER PUBLICATIONS

International Search Report for Application No. PCT/IB2019/057247, dated Dec. 26, 2019, 3 pages.

*Primary Examiner* — Ahmed M Farah
(74) *Attorney, Agent, or Firm* — Johnson & Johnson Surgical Vision, Inc.

(57) ABSTRACT

A narrow angle illumination light source for an ophthalmic surgical laser system includes multiple light emitting diodes (LEDs), multiple corresponding ball lenses, multiple corresponding upper apertures located between the LEDs and the lenses (optional), and multiple corresponding lower apertures located below the lenses. The light passing through each upper aperture and corresponding lens forms a light cone having a defined divergence angle and cone axis angle; the light cone only illuminates the corneal and sclera of a docked eye without illuminating the patients nose and orbit. The lower apertures may have distinctive shapes to aid video focusing. The multiple LEDs are distributed uniformly in the circle, and may be divided into multiple independently controllable segments which allows directional illumination.

(Continued)

The LEDs also have controllable brightness to allow images of darker and brighter illuminations to be taken in short succession.

20 Claims, 6 Drawing Sheets

(58) Field of Classification Search
CPC .......... A61F 9/00834; A61F 2009/0087; A61F 2009/00872; A61F 2009/00887; A61F 2009/00889
USPC ............................................ 606/4–6, 13, 17
See application file for complete search history.

(56) References Cited

U.S. PATENT DOCUMENTS

| | | | |
|---|---|---|---|
| 8,092,021 B1 * | 1/2012 | Northcott ............. | A61B 3/1015 351/221 |
| 8,132,912 B1 | 3/2012 | Northcott et al. | |
| 8,254,768 B2 | 8/2012 | Braithwaite et al. | |
| 8,345,936 B2 | 1/2013 | Burge et al. | |
| 8,502,968 B2 * | 8/2013 | Yavets-Chen .......... | G01N 21/55 356/237.2 |
| 9,335,101 B2 * | 5/2016 | Achammer ............. | F21K 9/233 |
| 9,836,648 B2 | 12/2017 | Perna et al. | |
| 2002/0159618 A1 | 10/2002 | Freeman et al. | |
| 2002/0159621 A1 * | 10/2002 | Callies ..................... | A61B 3/13 382/128 |
| 2011/0085137 A1 * | 4/2011 | Kleen ...................... | A61B 3/12 351/206 |
| 2012/0265181 A1 | 10/2012 | Frey | |
| 2013/0057828 A1 * | 3/2013 | de Smet .................. | A61B 3/12 351/207 |
| 2014/0055997 A1 | 2/2014 | Achammer et al. | |
| 2015/0146170 A1 * | 5/2015 | Su ........................... | A61B 3/14 351/206 |
| 2016/0095752 A1 | 4/2016 | Srinivasan et al. | |

FOREIGN PATENT DOCUMENTS

| | | |
|---|---|---|
| WO | 2010006176 A2 | 1/2010 |
| WO | 2012158825 A2 | 11/2012 |
| WO | 2015123440 A1 | 8/2015 |
| WO | 2016020147 A1 | 2/2016 |
| WO | 2017034701 A1 | 3/2017 |
| WO | 2017062162 A1 | 4/2017 |
| WO | 2017062235 A2 | 4/2017 |
| WO | 2017105608 A1 | 6/2017 |

* cited by examiner

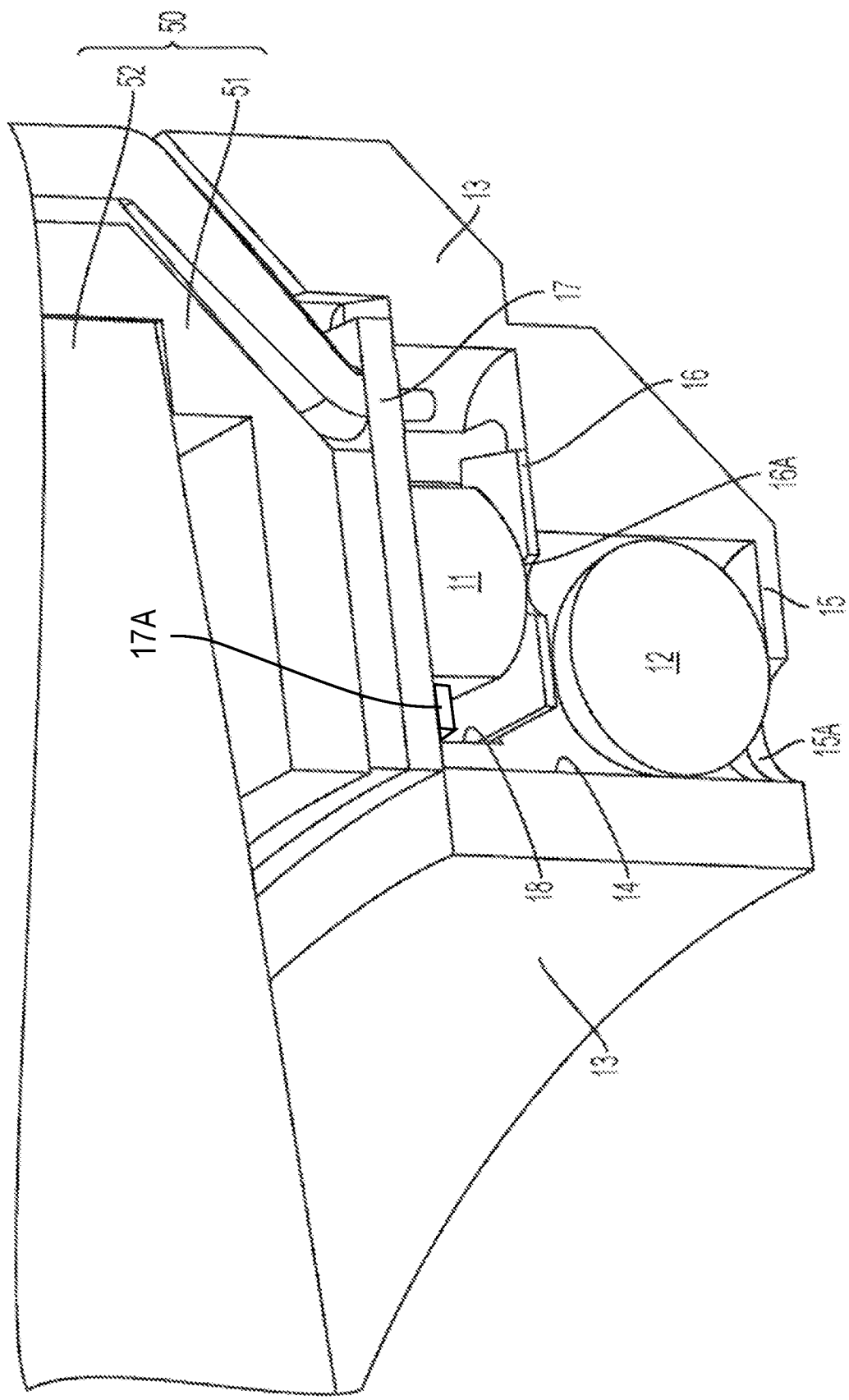

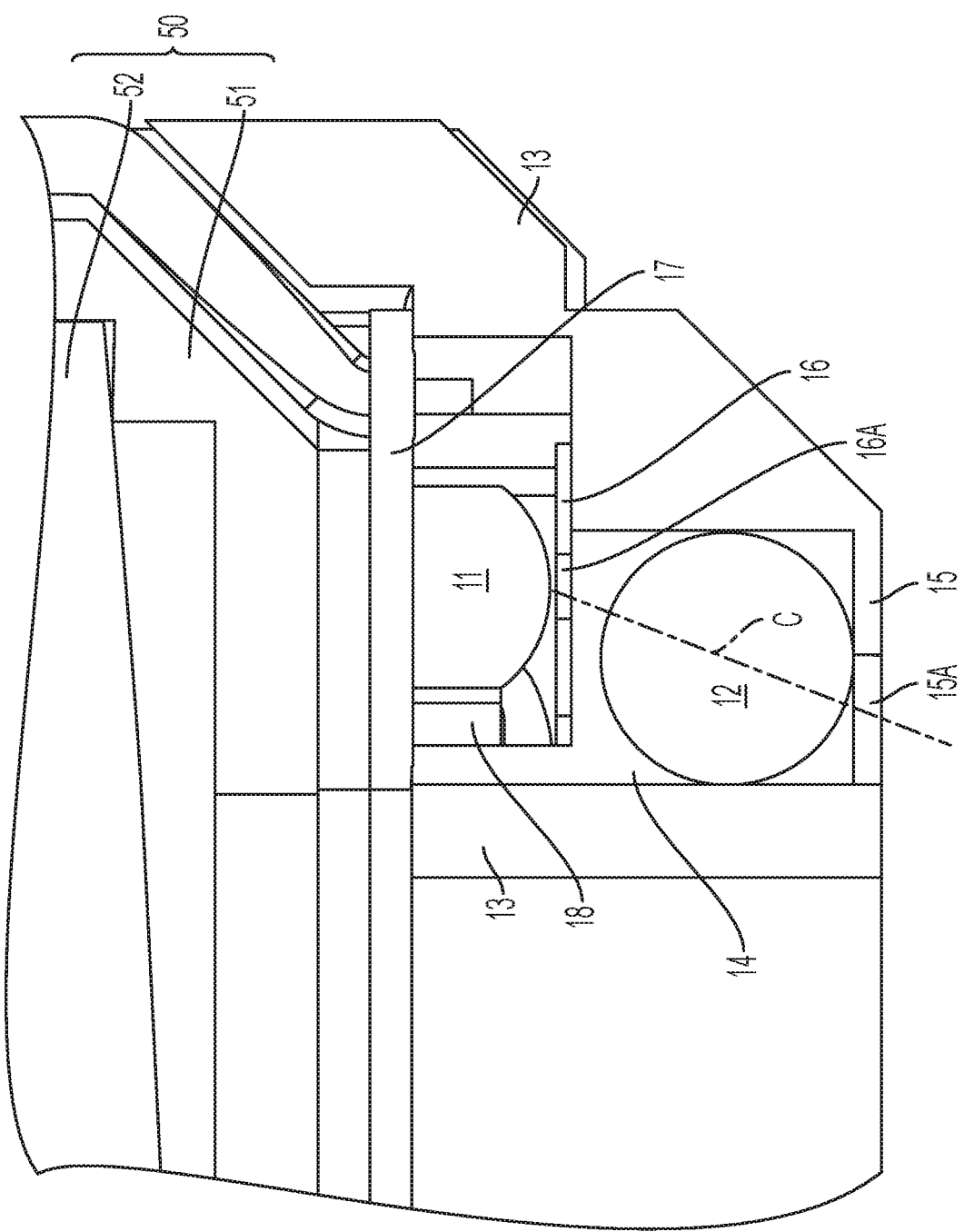

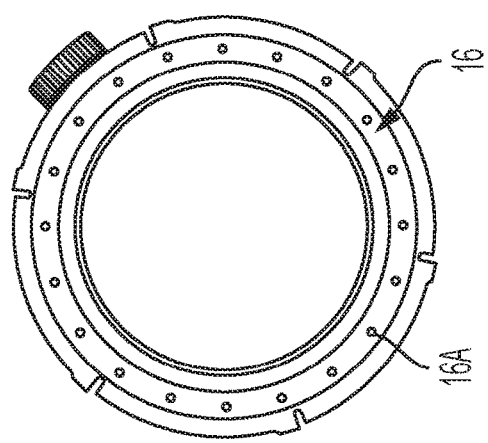
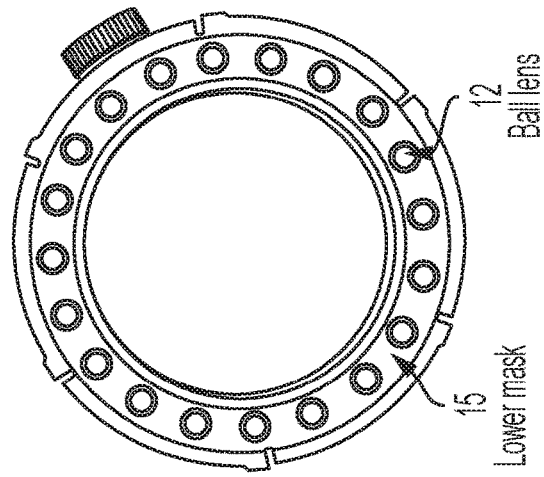
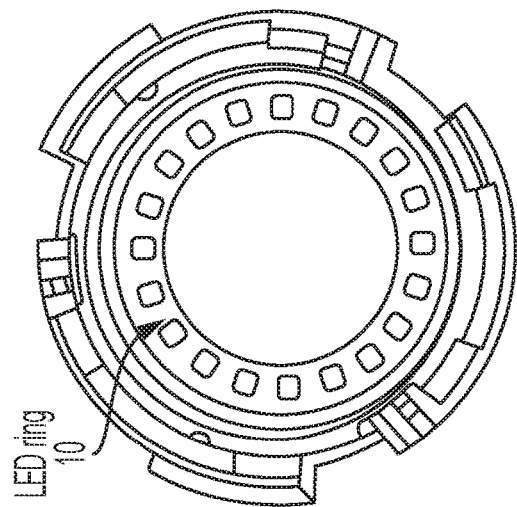
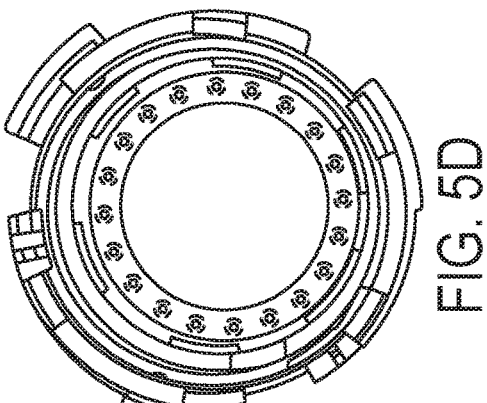
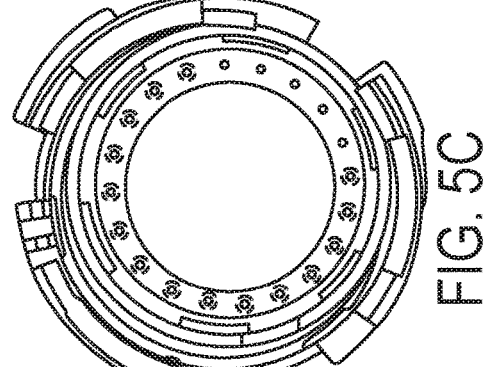
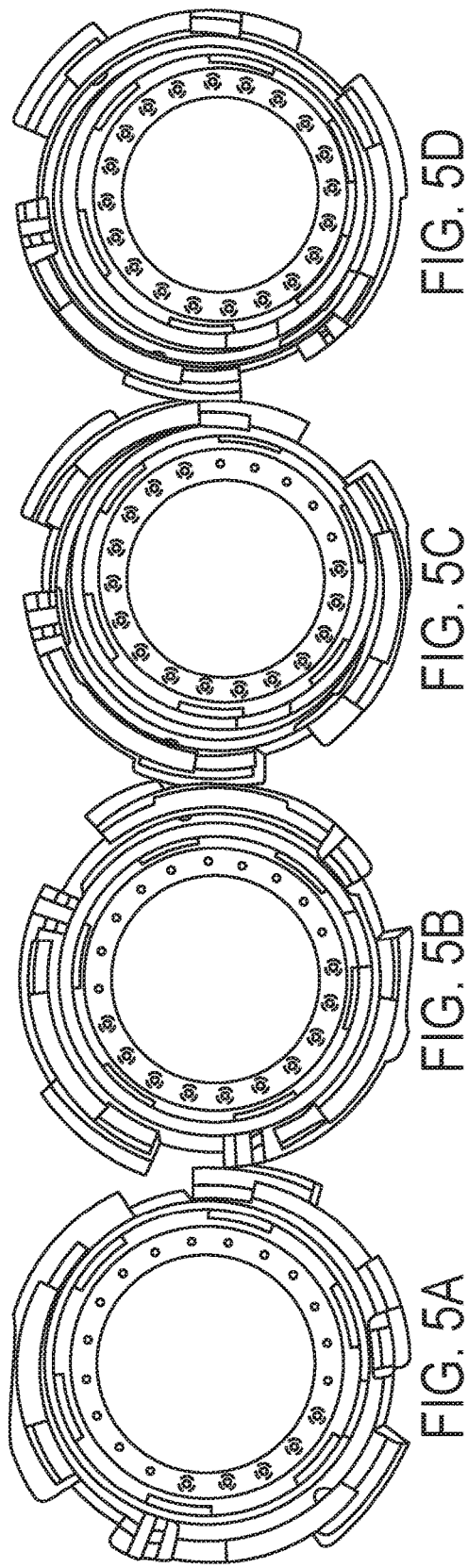

NARROW ANGLE ILLUMINATION RING FOR OPHTHALMIC SURGICAL LASER SYSTEM

CROSS REFERENCE TO RELATED APPLICATIONS

This application is a U.S. national stage of and claims the benefit under 35 U.S.C. § 371 of International Patent Application No. PCT/IB2019/057247, filed Aug. 28, 2019, which claims the benefit under 35 U.S.C. § 119(e) of U.S. Provisional Patent Application No. 62/726,939, filed Sep. 4, 2018, all of which are incorporated herein by reference in their entirety.

BACKGROUND OF THE INVENTION

Field of the Invention

This invention relates to an illumination device for an ophthalmic surgical laser system, and in particular, it relates to a narrow angle illumination device for corneal astigmatism measurement and iris registration, and other applications.

Description of Related Art

Ultrashort (e.g. femtosecond) pulsed laser systems are used to perform laser cataract procedures, which includes using the laser beam to make incisions on the surface of the eye such as the cornea or sclera, make incisions on the lens capsule, and fragment the lens for easy removal. An intraocular lens (IOL) is then implanted in the lens capsule. The same laser system may be used to correct corneal astigmatism while performing the cataract procedure, for example, by making arcuate relaxation incisions in the cornea or sclera to change the tension in the cornea, and/or by using a toric IOL and accurately aligning the IOL relative to the axis of corneal astigmatism. A patient's corneal astigmatism may be measured beforehand on a diagnostic device that is separate from the cataract laser system used to perform the cataract procedure. However, after docking the patient's eye to the cataract laser system (i.e. coupling the eye to the laser delivery head using a patient interface device), the actual orientation of corneal astigmatism may be different from that measured by the separate diagnostic device because of potential cyclorotation and docking induced rotation of the eye.

Conventional means of registering the patient's axis of astigmatism (e.g. the steep meridian of the cornea) to the coordinate frame of the cataract laser system include visually evaluating the eye using a video image of the eye taken by an onboard imaging system and manually placing ink marks on the eye. In another conventional method, the physician manually aligns fiducial features of the patient interface device to the patient's eye. Sometimes the possible rotations of the eye are simply ignored, and the axis of astigmatism is aligned the laser system's coordinate frame without compensation for cyclorotation and docking induced rotation of the eye.

Steep meridian registration technology (SMRT) is a technology that can accurately register the steep meridian of the patient's eye to the cataract laser system's coordinate system, enabling accurate placement and alignment of the relaxation incisions and/or the toric IOL. This technology requires measurement of the steep meridian referenced to an image of the iris, which in turn requires good iris image quality for registration. Some existing SMRT systems use internal illumination in the laser system and a placido mask attachment for astigmatism measurement and iris registration. A problem with existing SMRT technology is that the iris images have polarization artifacts, ghost images from the cataract laser system optics, and artifacts from the placido attachment. These image artifacts and ghosts can be erroneously identified as features of the iris, causing measurement and alignment errors. These problems can be partially solved by using an external illumination ring.

SUMMARY

Existing external illumination ring structure still has some problems. For example, ghost reflections from the patient's face (nose and orbit) are still present, and the field of illumination is too wide. The wide field of illumination illuminates the eyelids, causing eyelid images to be saturated, while the illumination on the iris is still not sufficient. These cause problems for iris feature identification during iris registration.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

Accordingly, the present invention is directed to an illumination light source for an ophthalmic surgical laser system, which includes: a ring shaped housing, having a plurality of lower apertures located in a bottom portion and forming a circle; a plurality of lenses disposed in a circle within the housing, each lens being located above one of the plurality of lower apertures; a ring shaped upper mask disposed within and concentrically with the housing, located above the plurality of lenses, the upper mask having a plurality of upper apertures formed thereon in a circle, each upper aperture being located above one of the plurality of lenses; a ring shaped circuit board disposed concentrically with the housing; and a plurality of light emitting devices disposed on the circuit board forming a circle, the plurality of light emitting devices located above the upper mask and having light emitting surfaces facing the upper mask, each light emitting device being locate above one of the upper apertures; wherein light emitted by each light emitting device, after passing through the corresponding upper aperture and focused by the corresponding lens, forms a light cone, wherein an axis of the light cone which passes through a center of the upper aperture and a center of the lens intersects a central axis of the housing at an intersection location which is at a predetermined distance from the lens, and wherein at the intersection location, a field of illumination of the light cone is between 10 mm and 20 mm in diameter.

In another aspect, the present invention is directed to an illumination light source for an ophthalmic surgical laser system, which includes: a ring shaped housing, having a plurality of apertures located in a bottom portion and forming a circle; a plurality of lenses disposed in a circle within the housing, each lens being located above one of the plurality of apertures; a ring shaped circuit board disposed concentrically with the housing; and a plurality of light emitting devices disposed on the circuit board forming a circle, each light emitting device being locate above, and having a light emitting surface facing, a corresponding one of the plurality of lenses; wherein light emitted by each light emitting device, after being focused by the corresponding lens, forms a light cone, wherein an axis of the light cone which passes through a center of the light emitting surface of the light emitting device and a center of the lens intersects a central axis of the housing at an intersection location which is at a predetermined distance from the lens, and wherein at the intersection location, a field of illumination of the light cone is between 10 mm and 20 mm in diameter.

In some embodiments, the plurality of light emitting devices are divided into a plurality of segments that can be independently controlled for on/off.

In some embodiments, the brightness of the light emitting devices are controllable.

In some embodiments, each lower apertures has a distinctive non-round shape.

It is to be understood that both the foregoing general description and the following detailed description are exemplary and explanatory and are intended to provide further explanation of the invention as claimed.

BRIEF DESCRIPTION OF THE DRAWINGS

FIG. 2 is a perspective cut-away view of one side of the illumination ring and a part of the laser delivery head.

FIG. 3 is a cross-sectional view of one side of the illumination ring and a part of the laser delivery head.

FIGS. 4A-4C illustrate the bottom views of the illumination ring and its components.

FIGS. 5A-5D illustrate the bottom view an of the illumination ring according to an embodiment of the present invention where the LEDs are divided into four quadrants.

DETAILED DESCRIPTION OF PREFERRED EMBODIMENTS

Embodiments of the present invention provide a narrow-angle illumination ring for an ophthalmic laser surgical system that improves iris image quality, thereby improving the registration of the corneal astigmatism axis to the iris. The illumination ring is an active external light ring permanently mounted on the delivery head of the laser system, without the use of a removable attachment. The narrow-angle illumination ring avoids the problem arising from polarization artifacts, ghost images from the laser system optics, and artifacts from the removable placido attachment used in previous systems. The narrow-angle illumination ring also limits the field of illumination to the patient's eye, so ghost reflections from the patient's face are effectively eliminated. The effects significantly improve iris image quality and the success rate of iris registration.

Figure 1:
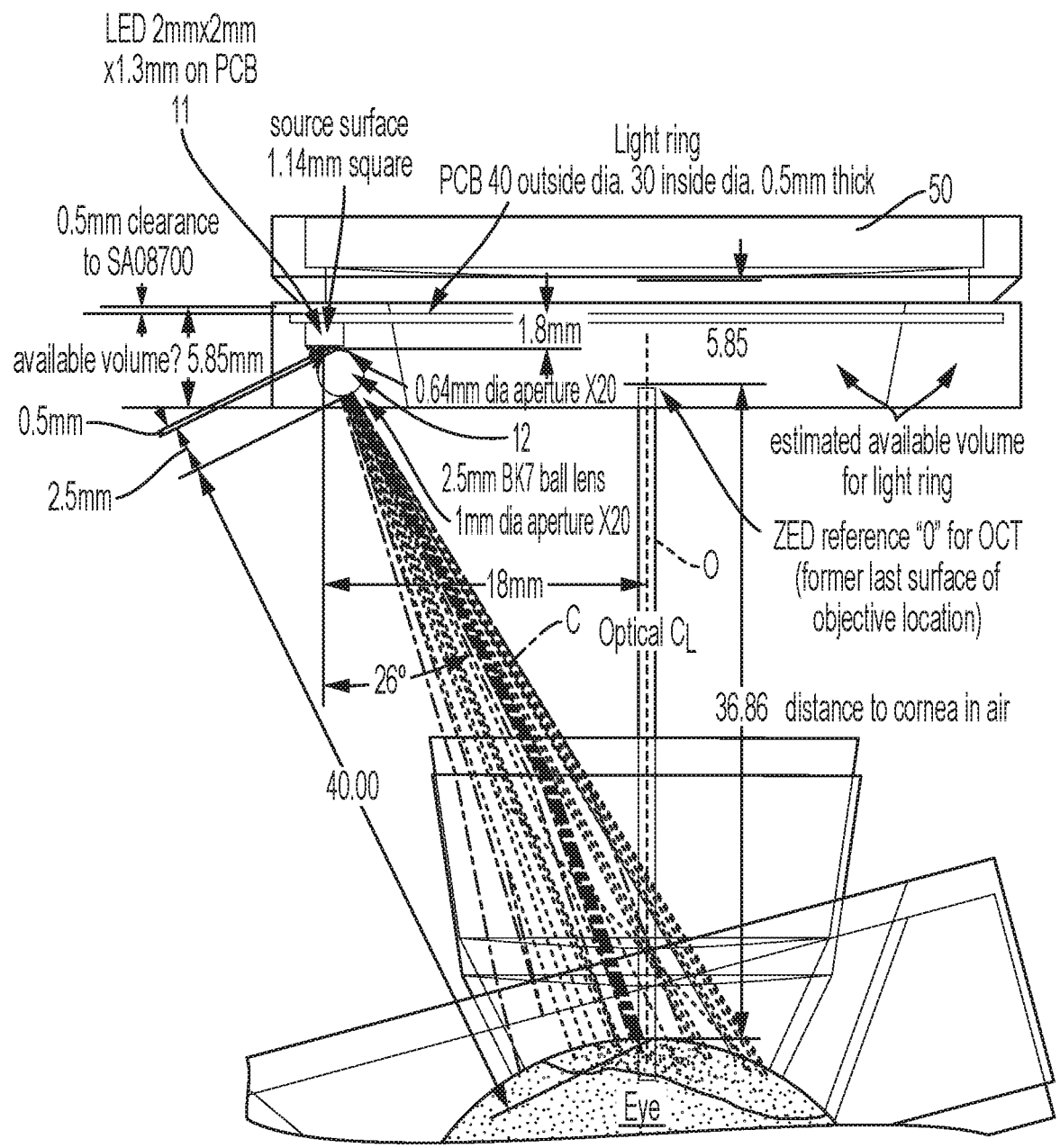
FIG. 1 schematically illustrates the overall arrangement of an illumination ring and its position on the laser delivery head according to an embodiment of the present invention.

FIGS. 1-4C schematically illustrate an illumination ring according to embodiments of the present invention. FIG. 1 is a cross-sectional view illustrating the overall geometry of the illumination ring and its position on the delivery head of the laser system (the LED on only one side is shown). FIG. 2 is a perspective cut-away view of one side of the illumination ring and a part of the laser delivery head. FIG. 3 is a cross-sectional view of one side of the illumination ring and a part of the laser delivery head. FIGS. 4A-4C illustrate the bottom views of the illumination ring and its components.

As shown in FIGS. 1-4C, the illumination ring 10 is mounted below and concentrically with the objective lens assembly 50 of the laser delivery head. A portion of the housing 51 and an optical element 52 of the objective lens assembly 50 are shown in FIGS. 2 and 3. The video camera used to capture images of the eye is not shown in the Figures, but they are well known in the art. In some embodiments, the video camera is disposed behind the objective lens with a beam splitter, and captures light reflected by the eye back to the objective lens.

The illumination ring 10 includes a ring shaped housing 13. The central opening defined by the ring shaped housing 13 is located below a central portion of the objective lens for passing the light between the objective lens and the patient's eye. In preferred embodiments, when the eye is docked to the laser delivery head, the illumination ring 10, along with a portion of the objective lens assembly 50, fits inside a cone shaped housing of the patient interface device.

The ring shaped housing 13 has a plurality cavities 14 arranged in a circle; a plurality of ball lenses 12 are partially or completely disposed in the cavities, forming a circle, with the top of the ball lenses exposed.

A plurality of light emitting diode (LED) devices 11 are arranged in a circle on a ring shaped printed circuit board (PCB) 17. The PCB 17 carrying the LEDs 11 is disposed concentrically with the housing 13, and upside-down above the ball lenses 12 so that the LEDs' light emitting surfaces face the ball lenses. An upper aperture mask 16, which is a ring shaped plate having a plurality of upper apertures 16A arranged in a circle, is disposed concentrically with the housing 13 and between the ball lenses 12 and the LEDs 11. In some embodiments, the upper aperture mask 16 and the LEDs are disposed in a ring shaped groove 18 of the housing 13. Further, a ring shaped bottom portion 15 of the housing 13 located below the ball lenses 12, referred to as the lower aperture mask 15, has a plurality of lower apertures 15A arranged in a circle, with each lower aperture located at the bottom of a corresponding cavity 14. The various components are made of light blocking materials and light can only pass through the apertures.

The plurality of LEDs 11, the plurality of upper apertures 16A in the upper aperture mask 16, the plurality of ball lenses 12, and the plurality of lower apertures 15A in the lower aperture mask 15 are equal in numbers, and are distributed in the respective circles in the same angular distribution and aligned with each other. Thus, each LED 11 is aligned in the radial direction (defined as a direction perpendicular to the central axis O of the ring shaped housing 13) with a corresponding upper aperture 16A, a corresponding ball lens 12, and a corresponding lower aperture 15A.

The light emitted by the LED 11 passes through the upper aperture 16A and is focused by the ball lens 12 to form a cone of light, where the axis C of the light cone passes through the center of the upper aperture and the center of the ball lens. In a cross-section passing through the central axis O, as illustrated in FIGS. 1 and 3, the angle of the axis C of the light cone with respect to the central axis O is determined by the relative positions of the upper aperture 16A and the ball lens 12, with the upper aperture serving as the source surface for the ball lens since the light emitting surface area of the LED 12 is larger than the upper aperture and disposed directly and immediately above the upper aperture. The center of the ball lens 12 is located closer to the central axis O than the center of the upper aperture 16A is, so the axis C of the light cone is slanted and points toward the central axis O. The center of the lower aperture is located closer to the central axis O than the center of the ball lens 12 is. In a preferred embodiment, the axis C of the light cone intersects the central axis O at a position approximately at the surface of the eye when the eye is docked to the laser delivery head. The divergence angle (i.e. the angular size) of the light cone is determined by the size of the upper aperture 16A, the focal length of the ball lens 12, and the distance between the upper aperture and the ball lens. The size of the lower aperture 15A affects the brightness of the light, but does not affect the angular size or axis angle of the light cone. The size and shape of the lower aperture 15A determines the size and shape of the image of the light source that will be formed by corneal reflection (the first Purkinje image), as will be discussed in more detail below.

In alternative embodiments, the upper aperture 16A is eliminated, and the light sources e.g. LED 11 are used directly above the ball lenses 12. Each light source has a light emitting area which has a desired size, faces the corresponding ball lens and is located at a desired position so as to form a desired light cone as described above.

The light cone's axis angle and angular size, along with the distance from the illumination ring to the eye, determine the field of illumination of the illumination ring. In preferred embodiments, as shown in FIG. 1, the light cone of each LED covers substantially the central portion of the eye, and the field of illumination of the plurality of LEDs substantially overlap each other. In preferred embodiments, the illumination ring is constructed to generate narrow-angle illumination where its field of illumination, at the location where the cone axis C intersects the central axis O of the housing (which is approximately located at the apex of the patient's eye when the eye is docked to the laser delivery head), is approximately between 10 mm and 20 mm in diameter, and more preferably, between 10 mm and 15 mm in diameter. The field of illumination may also be larger or smaller than the above ranges, so long as it adequately illuminates the patient's eye including the sclera and other structures inside of it and at the same time avoid illuminating the orbit and the nose. Nominally the limbus is approximately 12 mm in diameter, and it is desirable to illuminate slightly beyond the limbus, for example, at approximately 14 mm diameter. This field of illumination is limited to only the patient's eye (corneal and sclera), and will not illuminate the patient's nose and orbit. This can be achieved by selecting the various geometric parameters of the system.

Thus, an important consideration for the structure of the illumination ring 10 is to choose the parameters of the various components to achieve the desired field of illumination. To establish desired relative locations of the upper aperture 16A and the ball lens 12, in the embodiment shown in FIGS. 2 and 3, the ball lenses 12 are disposed in the cavities 14 of the housing, and the upper mask 16 is disposed in a groove of the housing. The cavities 14 and the groove 18 are sized to securely retain the ball lens 12 and the upper mask 16 in their respective positions. The radial position of the cavities 14 and the groove 18, the height of the bottom of the groove from the bottom of the cavities, the size and radial position of the upper apertures 16A, and the focal length of the ball lens 12 are designed to achieve predetermined angular size and axis angle of the light cone.

The optical geometry of the illumination ring in one particular example is shown in FIG. 1. In this example, the LED has a 1.14 mm×1.14 mm light emitting surface; the upper aperture is 0.64 mm in diameter; the ball lens is 2.5 mm in diameter and made of BK7 glass; the upper aperture is located at 0.5 mm from the surface of the ball lens; the lower aperture is 1 mm in diameter; the radial distance from the center of the upper aperture to the central axis is 18 mm; the angle between the light cone's axis and the central axis is 26 degrees; the angular size of the light cone is approximately 7-14 degrees (half angle); and the oblique distance from the lower aperture to the apex of the cornea is 40 mm. All of the above values are approximate.

Figure 6A:
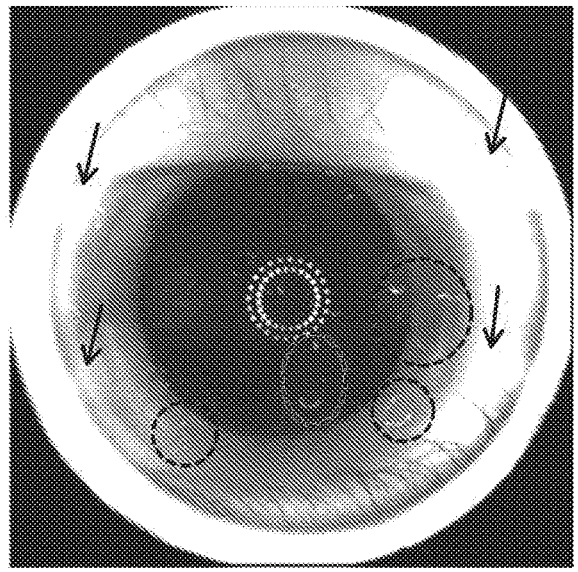
FIGS. 6A-6F show iris images captured using different illumination configurations.
Figure 6B:
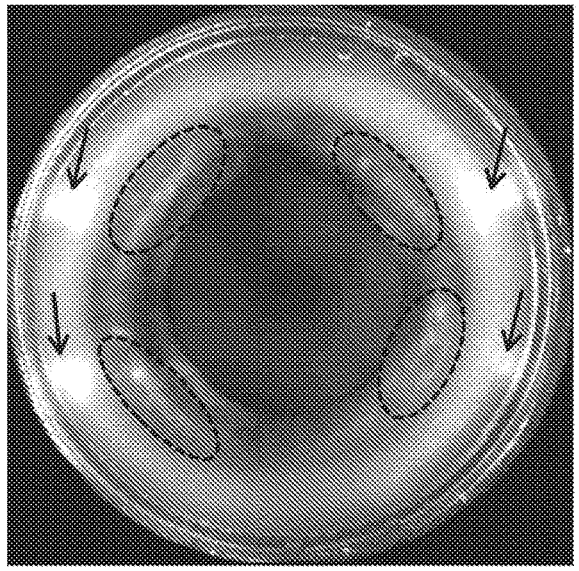
Figure 6C:
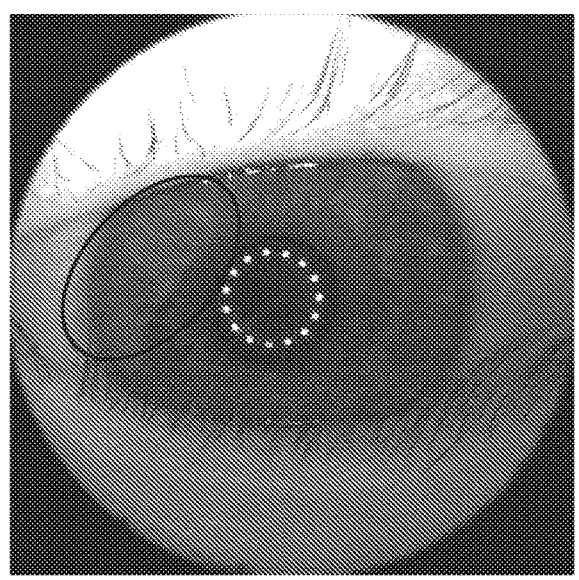
Figure 6D:
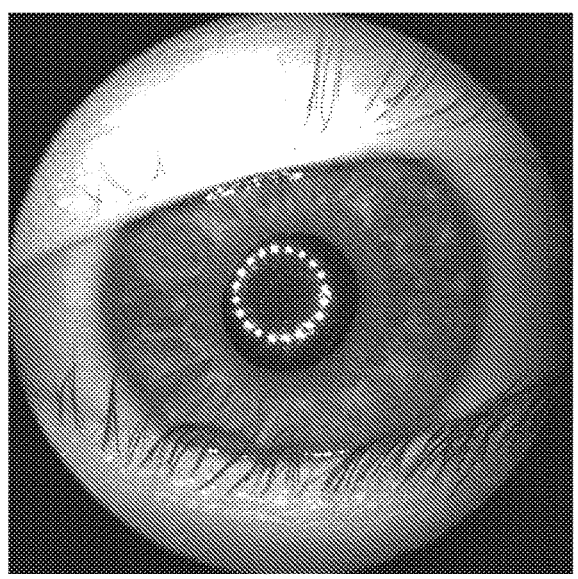
Figure 6F:
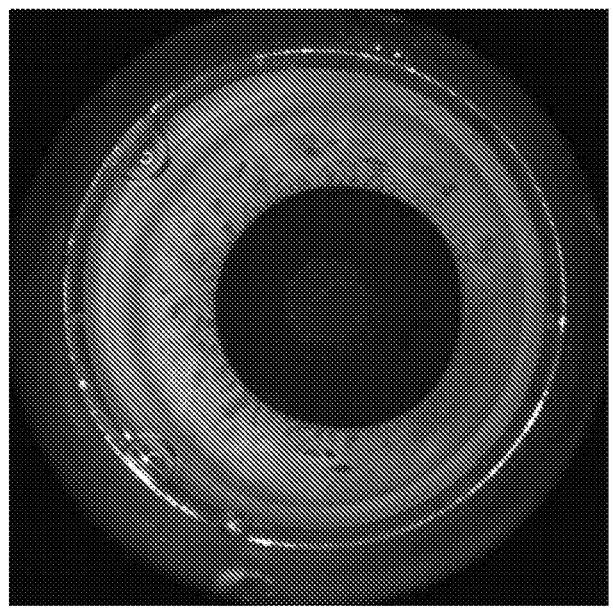
Figure 6E:
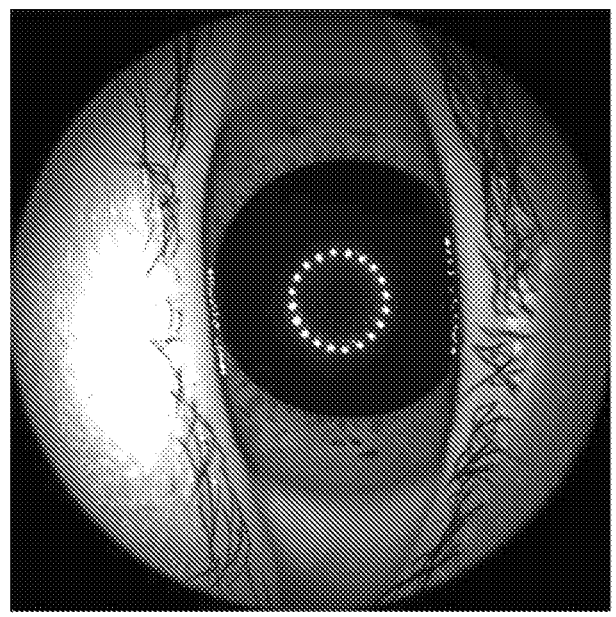

FIGS. 6A-6F show iris images captured using different illumination configurations. FIGS. 6A, 6C and 6E are images taken in air (i.e. without patient interface) using a known placido mask attachment (FIG. 6A), a wide-angle illumination ring (FIG. 6C), or a narrow-angle illumination ring of one embodiment of the present invention (FIG. 6E). FIG. 6B is a corresponding docked image using the placido mask illumination. FIG. 6F is a corresponding docked image using the narrow-angle illumination ring. In the docked images, the cornea is index matched by the water bath in the patient interface so the first and second Purkinje images are extremely faint. FIG. 6D is another image taken in air using the narrow-angle illumination ring for comparison with FIG. 6C (wide-angle illumination). Since the narrow-angle illumination ring limits the field of illumination, the ghost reflection from nose (marked by the ellipse) in FIG. 6C is eliminated. The narrow-angle illumination better balances the intensity on iris and eyelids, to provide higher contrast of the iris portion, and less saturation of the eyelid portion. The image in FIG. 6D has the advantage of better iris feature identification as well as more reliable iris registration (compared to FIG. 6C).

In FIGS. 6A and 6B, ghost images from internal surfaces in the laser delivery hear are marked by arrows. Artifacts due to dust on the placido attachment are marked by dotted line ellipses in FIG. 6A. Polarization artifacts from the interaction of the internal illumination of the laser head with the eye are shown by dotted ellipses in FIG. 6B. The ghost reflection with wide-angle illumination is marked by an ellipse in FIG. 6C. All of these ghosts and artifacts are eliminated in FIGS. 6D and 6E using narrow-angle illumination It should be noted that the narrow-angle illumination ring is particularly advantageous for iris registration. The same narrow-angle illumination ring is used for corneal astigmatism measurement by measuring Purkinje images, although the narrow-angle feature does not significantly improve such measurement. Nonetheless, since the iris image is used to register the axis of astigmatism to the iris image, high quality iris image improving iris registration for the axis of astigmatism.

In the example shown in FIGS. 4A-4C, the illumination ring has twenty LEDs and the same number of upper apertures, ball lenses and lower apertures, but other numbers may be used. In preferred embodiments, the LEDs and the corresponding apertures and lenses are distributed uniformly in the angular direction, but non-uniform angular distributions may be used.

As mentioned above, the illumination ring provide the light sources for both iris imaging and the imaging of Purkinje reflections which is used to measure astigmatism. Several additional features of the illumination ring provides further advantages in these imaging processes.

One feature is the independent control of individual LEDs or groups of LEDs. In some embodiment, the plurality of LEDs are divided into a number of segments that can be independently controlled to be turned on/off and to adjust their brightness. The control is accomplished by suitable LED drive circuits 17A (see FIG. 2) which may be disposed either on the PCB 17 or elsewhere in the system. In one embodiment, the LEDs are divided into four quadrants, as shown in FIGS. 5A-5D, where one to four quadrants are turned on, respectively. In another embodiment, each individual LED is a segment that can be independently controlled.

Such independently controllable LED segments enable the control of illumination direction and intensity. One application of independently controllable LED segments is to generate angled illumination, by turning on only some of the LEDs, so as to create shadows that highlight the reliefs of the features of the iris.

Another feature is the controllable brightness of the LEDs. In some embodiments, the brightness of the LEDs can be rapidly varied so as to capture video images under different illumination levels. The darker images can be used to measure the Purkinje image, i.e. image of the light source reflected from the cornea, in this case a ring shaped dot pattern. This is because in the darker images the light dots of the Purkinje image are less saturated so their center positions can be more accurately measured. The Purkinje measurement are used to determine astigmatism of the cornea. Thus, using darker images can enhance the accuracy and resolution of corneal measurement. On the other hand, the brighter images allows for higher quality iris images. A series of images of different illumination levels may be taken within a short time frame, for example less than a second, and analyzed in the above manner, and the measured axis of astigmatism can then be registered to the iris image.

Another feature is the distinctive shapes of the lower apertures which can assist in focusing of the video camera. In some embodiments, the lower apertures 15A of the illumination ring 10 are formed of predefined distinctive shapes that are non-round, such as squares, triangles, stars, etc. to aid in focusing the video camera on the eye. When focusing the video camera, the shape of the focus spot in the video images are observed to determine whether their shapes resemble the known shapes of the lower apertures. When the video camera is well focused, the shape of the dots of the image becomes a substantially identical to that of the lower apertures. Also, by using specific distinctive shapes of the lower aperture, the shapes in the video image can be more easily recognized by computer vision techniques.

Those skilled in the art will recognize that various changes may be made to the above-described embodiments. For example, in preferred embodiments, ball lenses as the lens 12 are used because ball lenses help to make the light distribution within the cone more uniform. In alternative embodiments, other types of lenses may be used.

In alternative embodiments, the plurality of ball lenses may be formed integrally as one piece, for example by injection molding. In such a structure, the cavities 14 may not be necessary or may have other shapes.

In preferred embodiments, the various components of the illumination ring 10 are assembled into a one-piece ring shaped component, and the one piece component is then mounted on the front of the objective. In other embodiments, various components may be formed into different assemblies or modules first, and then sequentially assemble together on the laser delivery head.

In some embodiments, the LEDs generate light at 735 nm wavelength, but other wavelengths may be used. Also, other light sources than LEDs may be used.

It will be apparent to those skilled in the art that various modification and variations can be made in the narrow-angle illumination ring apparatus and related method of the present invention without departing from the spirit or scope of the invention. Thus, it is intended that the present invention cover modifications and variations that come within the scope of the appended claims and their equivalents.

What is claimed is:

1. An illumination light source for an ophthalmic surgical laser system, comprising:
   a ring shaped housing, having a plurality of lower apertures located in a bottom portion and forming a circle;
   a plurality of lenses disposed in a circle within the housing, each lens being a focusing lens and located above one of the plurality of lower apertures;
   a ring shaped upper mask disposed within and concentrically with the housing, located above the plurality of lenses, the upper mask having a plurality of upper apertures formed thereon in a circle, each upper aperture being located above one of the plurality of lenses;
   a ring shaped circuit board disposed concentrically with the housing; and
   a plurality of light emitting devices disposed on the circuit board forming a circle, the plurality of light emitting devices located above the upper mask and having light emitting surfaces facing the upper mask, each light emitting device being located above one of the upper apertures;
   wherein light emitted by each light emitting device, after passing through the corresponding upper aperture and focused by the corresponding lens, forms a light cone, wherein an axis of the light cone which passes through a center of the upper aperture and a center of the lens intersects a central axis of the housing at an intersection location which is at a predetermined distance from the lens, and wherein at the intersection location, a field of illumination of the light cone is between 10 mm and 20 mm in diameter.

2. The illumination light source of claim 1, wherein the housing defines a plurality of cavities arranged in a circle, wherein each lens is disposed within one of the plurality of cavities and each lower aperture is located at a bottom of a corresponding cavity.

3. The illumination light source of claim 1, wherein the housing further defines a ring shaped groove, and wherein the upper mask and the plurality of light emitting devices are disposed within the ring shaped groove.

4. The illumination light source of claim 1, wherein each lens is a ball lens.

5. The illumination light source of claim 1, wherein each lens is a ball lens, and wherein the plurality of lenses are formed integrally into one piece.

6. The illumination light source of claim 1, wherein of the plurality of light emitting devices are disposed uniformly in an angular direction around the central axis.

7. The illumination light source of claim 1, wherein the plurality of light emitting devices are divided into a plurality of segments, the illumination light source further comprising circuitry for independently controlling on/off states of each segment.

8. The illumination light source of claim 1, further comprising circuitry for controlling a brightness of each light emitting devices.

9. The illumination light source of claim 1, wherein each of the plurality of lower apertures has a non-round shape.

10. The illumination light source of claim 1, wherein the housing, the lenses, the upper mask, the circuit board, and the light emitting devices form a one-piece component configured to be permanently mounted on the ophthalmic surgical laser system.

11. An illumination light source for an ophthalmic surgical laser system, comprising:
   a ring shaped housing, having a plurality of apertures located in a bottom portion and forming a circle;

a plurality of lenses disposed in a circle within the housing, each lens being a focusing lens and located above one of the plurality of apertures;

a ring shaped circuit board disposed concentrically with the housing; and a plurality of light emitting devices disposed on the circuit board forming a circle, each light emitting device being located above, and having a light emitting surface facing, a corresponding one of the plurality of lenses;

wherein light emitted by each light emitting device, after being focused by the corresponding lens, forms a light cone, wherein an axis of the light cone which passes through a center of the light emitting surface of the light emitting device and a center of the lens intersects a central axis of the housing at an intersection location which is at a predetermined distance from the lens, and wherein at the intersection location, a field of illumination of the light cone is between 10 mm and 20 mm in diameter.

12. The illumination light source of claim 11, wherein the housing defines a plurality of cavities arranged in a circle, wherein each lens is disposed within one of the plurality of cavities and each aperture is located at a bottom of a corresponding cavity.

13. The illumination light source of claim 11, wherein the housing further defines a ring shaped groove, and wherein the plurality of light emitting devices are disposed within the ring shaped groove.

14. The illumination light source of claim 11, wherein each lens is a ball lens.

15. The illumination light source of claim 11, wherein each lens is a ball lens, and wherein the plurality of lenses are formed integrally into one piece.

16. The illumination light source of claim 11, wherein of the plurality of light emitting devices are disposed uniformly in an angular direction around the central axis.

17. The illumination light source of claim 11, wherein the plurality of light emitting devices are divided into a plurality of segments, the illumination light source further comprising circuitry for independently controlling on/off states of each segment.

18. The illumination light source of claim 11, further comprising circuitry for controlling a brightness of each light emitting devices.

19. The illumination light source of claim 11, wherein each of the plurality of apertures has a non-round shape.

20. The illumination light source of claim 11, wherein the housing, the lenses, the circuit board, and the light emitting devices form a one-piece component configured to be permanently mounted on the ophthalmic surgical laser system.

* * * * *